United States Patent
Nau et al.

(10) Patent No.: US 6,274,624 B1
(45) Date of Patent: Aug. 14, 2001

(54) ANTIPROLIFERATIVE AND NEUROTROPHIC MOLECULES

(75) Inventors: Heinz Nau, Berlin (DE); Ciaran M. Regan, Dublin (IE)

(73) Assignee: American Biogenetic Sciences Inc., Copiague, NY (US)

( * ) Notice: Subject to any disclaimer, the term of this patent is extended or adjusted under 35 U.S.C. 154(b) by 0 days.

(21) Appl. No.: 09/075,887

(22) Filed: May 11, 1998

Related U.S. Application Data (60) Division of application No. 08/446,481, filed on May 22, 1995, which is a continuation-in-part of application No. 08/298,108, filed on Aug. 30, 1994, now Pat. No. 5,672,746.

(51) Int. Cl.[7] .......................... A01N 37/00; A61K 31/19; C07C 57/02; C07C 57/18
(52) U.S. Cl. ......................... 514/557; 514/558; 562/598
(58) Field of Search ........................... 562/598; 514/557, 514/558

(56) References Cited

FOREIGN PATENT DOCUMENTS

| | | |
|---|---|---|
| 1066578 | 10/1959 | (DE) . |
| WO 94/06743 A1 * | 3/1994 | (DE) . |

OTHER PUBLICATIONS

Reference to Schulte of DE 1066578 1959.*
Reference to Arch. Pharm. (Weinheim Ger.), 291 <1958>227,233, 1958.*

Nau et al., "Valproic Acid–Induced Neural Tube Defects in Mouse and Human: Aspects of Chirality, Alternative Drug Development, P harmacokinetics and Possible Mechanisms", Pharmacology & Toxicology 69, pp. 310–321, 1991.*

Claude Lambert, et al., 1984, *Tetrahedron Letters*, 25:5323–5326 "Palladium (II) Catalyzed Cyclization of Alkynoic Acids".

Robin W. Spencer, et al., 1986, *J. Am. Chem. Soc.*, 108:5589–5597 "Ynenol Lactones: Synthesis and Investigation of Reactions Relevant to Their Inactivation of Serine Proteases".

George R. Negrete, et al., 1991, *Tetrahedron: Asymmetry*, 2:105–108 "Asymmetric Alkylations of N–Acyl Dihydropyrimidionones".

Karl E. Schulte et al., 1958, *Arch. Pharm.*, 291:227–237 "Acetylene Carboxylic Acids—(IX) Formation of Unsaturated Lactones from Alkyne Acids".

* cited by examiner

Primary Examiner—Dwayne C. Jones
(74) Attorney, Agent, or Firm—Morgan & Finnegan LLP (57) ABSTRACT

Neurotrophic and antiproliferative compounds related to the antiepileptic drug valproate are provided. These compounds are useful for promoting neuronal function as in neurodegenerative disorders and for treating neoplastic disease.

3 Claims, 7 Drawing Sheets

| | Treatment | Protocol |
|---|---|---|
| 1 | vehicle: 0.5mls 0.9% (w/v) saline | vehicle 3hr + vehicle 6hr (n=7) |
| 2 | vehicle: 0.5mls 0.9% (w/v) saline<br>drug: scopolamine 0.8 mg/kg ip | vehicle 3hr + scopolamine 6hr (n=8) |
| 3 | drug: 2-n-pentyl-4-pentynoic acid<br>16.8 mg/kg ip<br>drug: scopolamine 0.8mg/kg ip | 2-n-pentyl-4-pentynoic acid 3hr +<br>scopolamine 6hr (n=5) |
| 4 | drug: 2-n-pentyl-4-pentynoic acid<br>50.4 mg/kg ip<br>drug: scopolamine 0.8mg/kg ip | 2-n-pentyl-4-pentynoic acid 3hr +<br>scopolamine 6hr (n=6) |
| 5 | drug: 2-n-pentyl-4-pentynoic acid<br>84.0 mg/kg ip<br>drug: scopolamine 0.8 mg/kg ip | 2-n-pentyl-4-pentynoic acid 3hr +<br>scopolamine 6hr (n=6) |
| 6 | drug: 2-n-pentyl-4-pentynoic acid<br>134.0 mg/kg ip<br>drug: scopolamine 0.8 mg/kg ip | 2-n-pentyl-4-pentynoic acid 3hr +<br>scopolamine 6hr (n=6) |
| 7 | drug: 2-n-pentyl-4-pentynoic acid<br>50.4 mg/kg ip<br>vehicle: 0.5 mls 0.9% (w/v) saline | 2-n-pentyl-4-pentynoic acid 3hr +<br>vehicle 6hr (n=3) |
| 8 | drug: 2-n-pentyl-4-pentynoic acid<br>84.0 mg/kg ip<br>vehicle: 0.5 mls 0.9% (w/v) saline | 2-n-pentyl-4-pentynoic acid 3hr +<br>vehicle 6hr (n=3) |
| 9 | drug: 2-n-pentyl-4-pentynoic acid<br>134.0 mg/kg ip<br>vehicle: 0.5 mls 0.9% (w/v) saline | 2-n-pentyl-4-pentynoic acid 3hr +<br>vehicle 6hr (n=4) |

Dentate gyrus

Rhinal cortex

ANTIPROLIFERATIVE AND NEUROTROPHIC MOLECULES

REFERENCE TO RELATED APPLICATIONS

This application is a divisional of application Ser. No. 08/446,481 filed May 22, 1995 (which is incorporated herein by reference), which is a continuation-in-part of U.S. patent application Ser. No. 08/298,108, filed Aug. 30, 1994, now U.S. Pat. No. 5,672,746 which is incorporated herein by reference.

FIELD OF THE INVENTION

This invention provides methods and compositions useful for the prevention and/or treatment of neurodegenerative and proliferative diseases. The compositions of the invention promote neuronal cell maturation and retard their proliferation. In particular, this invention relates to nonprotein neurotrophic molecules capable of passing the blood brain barrier to provide therapeutic effects.

BACKGROUND

Proper function of the nervous system requires the maturation and maintenance of neuronal cells. In addition, the establishment of proper synaptic connections allows for the communication between different neurons. Deficits in the survival of neurons, or the ability to maintain synaptic connections is associated with neurodegenerative disorders including Alzheimer's disease, Huntington's disease, amyotrophic lateral sclerosis (ALS), Parkinson's disease, stroke and degeneration of neurons due to diabetic neuropathy and trauma.

Many of the neurodegenerative disorders are associated with the loss or degeneration of a particular class of neuronal cells. For example, in Parkinson's disease dopaminergic neurons of the substantia nigra degenerate. Whereas ALS is associated with the loss of motor neurons. Wernicke-Korsakoff syndrome, commonly associated with chronic alcoholism, causes amnesia due to damage to the mammillary bodies and medial dorsal nucleus of the thalamus. Butters N., *Seminar Neurol.* (1984) 4:226–244. Alzheimer's disease appears to be associated with the degeneration of certain cholinergic neurons. The severance of axons as a result of trauma may cause retrograde degeneration and neuronal death.

The association between neurodegeneration and the development of disease has prompted the search for neurotrophic agents capable of retarding, preventing, or reversing such neurodegeneration. To date, much emphasis in this area has focused on the identification and characterization of neurotrophic polypeptides. For example, attention has been given to studying the effects of nerve growth factor (NGF), ciliary neurotrophic factor (CNTF), brain drive neurotrophic factor (BDNF) and others. The general neurotrophic effect of CNTF and, in particular, its trophic action on motor neurons has led to its investigation as a useful agent in the treatment of ALS and other neurodegenerative disorders. See, for example, Collins et al. U.S. Pat. No. 5,141,856 and Masiakowski WO 91/04316 which are incorporated herein by reference. NGF which has been shown to promote neuronal outgrowth from central cholinergic neurons has been suggested as a useful agent in the treatment of Alzheimer's disease. Most of the neurotrophic polypeptides identified to date are active on relatively restricted populations of neuronal cells. Whereas others such as CNTF are active on a greater number of neuronal cell types.

It has generally been observed that agents which induce maturation or differentiation of neuronal cells in culture, also inhibit their proliferation. Normal proliferating embryonic precursors to sympathetic and sensory neurons are induced to mature and stop dividing in the presence of certain growth factors such as NGF. The association between neuronal maturation or differentiation and anti-mitotic action has also been observed for certain neoplastic cells which are responsive to neurotrophic factors. For example, rat pheochromocytoma, PC12, cells in the presence of NGF develop long neurites and stop dividing. Green L A and Tischler A S, *Proc. Natl. Acad. Sci. USA* (1976) 72:2424–2428. Similar effects have been observed with other neuronal cells.

Cells in the nervous system give rise to a variety of potentially fatal neoplastic diseases. For example, neuroblastoma and pheochromocytoma are believed to arise from cells having an origin in the neural crest. Non-neuronal cells of the nervous system including glial cells, astrocytes and Schwann cells also give rise to different types of tumors. Most present agents used for chemotherapy involving neuronal cells are cytotoxic and have relatively poor specificity and penetrability. Treatment of neoplastic disease through agents causing maturation has been a long sought for goal. Aaronson, S. A. *Science* (1991) 254:1146–1153.

Although neurotrophic polypeptides may eventually prove useful for treating certain neurodegenerative, and proliferative disorders, they are characterized by poor bioavailability resulting from their relatively large size making them resistant to passing through the blood brain barrier. This poor penetration into the relevant target tissue raises substantial difficulties in their use for treating neurodegenerative disorders and neoplastic disease of the central nervous system.

The anticonvulsant sodium valproate (VPA) is a branched chain carboxylic acid effective in the treatment of primary generalized seizures, especially those of the absence type. Pinder, R. M. et al., *Drugs* (1977) 13:81–123. Recently, VPA has been reported to be a teratogen and has been suggested as potentially causing neural tube defects in 1% to 2% of exposed fetuses (Robert E. and Rosa F. W., "Maternal valproic acid and neural tube defects," *Lancet* (1982) 2:937). In addition, a number of other defects are also induced by valproic acid treatment during pregnancy (Nau et al. *J. Pharmacol. Exp. Ther.* (1981) 219:768–777. Spina bifida aperta, a most serious birth defect, can now also be induced by valproic acid in an animal model (Ehlers et al., 1992 a,b). Like the neurotrophic polypeptides, valproic acid also shows very limited transfer into the central nervous system of the human (Löscher et al., *Epilepsia* (1988) 29:311–316). For reviews of clinical and experimental valproic acid teratogenesis. cf. Nau et al., *Pharmacol. Toxicol.* (1991) 69:310–321; Nau, *CIBA Foundation Symposium* 181, pp. 615–664; Marcel Dekker, 1993.

Studies in vitro have demonstrated valproate to potently inhibit the rate of neural derived cell proliferation at concentrations within its therapeutic plasma level (Regan, C., *Brain Res.* (1985) 347:394–398). This antiproliferative action of valproate is restricted to a defined point in the $G_1$ phase of the cell cycle. Martin M. and Regan C., *Brain Res.* (1991) 554:223–228. In the presence of valproate, cells assume a differentiated phenotype as judged by morphology, increased cell-substratum adhesivity and decreased affinity for concanavalin A lectin coated surfaces (Martin et al., *Toxic in Vitro* (1988) 2:43–48; Martin et al., *Brain Res.* (1988) 459:131–137; Maguire and Regan, *Int. J. Devl. Neurosci.* (1991) 9:581–586; Regan, C., *Brain Res.* (1985)

347:394–398. These actions of valproate are likely to be restricted to cells of the developing neural tube as, in in vivo experimental models, valproate has been shown to increase the incidence of neural tube defects and sequester specifically into the neuroepithelium where it generates cellular disarray (Dencker et al., *Teratology* (1990) 41:699–706; Ehlers et al., *Teratology* (1992) 45:145–151; Ehlers et al., *Teratology* (1992) 46:117–130; Kao et al., *Teratogen. Mutagen. Carcinogen.* (1981) 1:367–382; Turner et al., *Teratology* (1990) 41:421–442.

Hyperthermia, which induces neural tube defects (Chernoff and Golden, *Teratology* (1988) 37:37–42; Edwards, *Teratogen. Mutagen. Carcinogen.* (1986) 6:563–582; Shiota, *Am J. Med. Genet.* (1982) 12:281–288; Finnell et al., *Teratology* (1986) 33:247–252), also arrests neural cells in the $G_1$ phase of the cell cycle both in vivo and in vitro (Martin et al. *Brain Res.* (1991) 554:223–228; Walsh and Morris, *Teratology* (1989) 40:583–592); and produces similar pro-differentiative effects to those observed with valproate (Martin and Regan, *Brain Res.* (1988) 459:131–137). Thus, a coincident anti-proliferative and pro-differentiative action may identify agents which are capable of inducing neural tube defects yet provide a basis for the development of compounds useful for treatment or prevention of neurodegenerative diseases.

The studies of the structure activity relationship of teratogenic valproate-related compounds suggest a strict structural requirement for high teratogenic potency. Nau, H. et al., *Pharmacol. & Toxicol.* (1991) 69:310–321. Studies of structure-activity relationships were possible as a result of previous work demonstrating that the parent drug molecule—at least in the case of valproic acid—and not metabolite(s) proved responsible for the teratogenic action (Nau, *Fundam Appl Toxicol*, (1986) 6:662–668. Molecules which are highly teratogenic were reported to require an alpha-hydrogen atom, a free carboxyl function, and branching on carbon atom 2 with two chains containing three carbons each for maximum teratogenic activity. (Nau and Löscher, 1986; Nau and Scott, 1986). Substances which do not conform with these strict structural requirements are of very low or negligible teratogenic activity, but still often exhibit good anticonvulsant activity in several experimental models. These compounds may therefore be valuable anti-epileptic agents (Nau et al., Neurology (1984) 34:400–402; Löscher and Nau, *Neuropharmacol* (1985) 24:427–435; Wegner and Nau, *Neurology* (1992) 42 (Supp. 5):17–24; Elmazar et al., *J. Pharm. Sci.* (1993) 82:1255–1258. Teratogenic activity also demonstrated stereoisomeric preferences suggesting a stereoselective interaction between the drugs and a specific structure within the embryo.

In the case of 4-en-VPA (2-n-propyl-4-pentenoic acid) (Hauck and Nau, *Toxicol Lett* (1989) 49:41–48) and 4-yn-VPA (2-n-propyl-4-pentynoic acid) (Hauck and Nau, *Pharm. Res.* (1992) 9:850–855) the S-enantiomers proved to be more potent teratogens than the corresponding R-enantiomers. This stereoselective teratogenicity was due to differing intrinsic teratogenic potencies of the enantiomers, and not due to differences in pharmacokinetics as both enantiomers of a given pair reached the target tissue to the same degree, but one was more potent than the other (Hauck et al., *Toxicol. Lett* (1992) 60:145–153). Other examples supported the pronounced stereoselectivity of the teratogenic, but not the anticonvulsant and sedative effect (Hauck et al., *Life Sci.* (1990) 46:513–518; Nau et al., *Pharmacol. & Toxicol.* (1991) 69:310–321. Carbon chains connected to carbon atom 2 of valproate which were shorter or longer than 3 carbons reduced teratogenic activity. Nau et al. Id. Valproate's antimitotic activity has been suggested as being related to its teratogenic potential rather than as a potential therapeutic asset, as the non-teratogenic valpromide analogue is not antiproliferative (Regan et al., *Toxic in Vitro* (1991) 5:77–82). Teratogenic analogs of valproate have been synthesized to date for the purpose of producing more desirable antiepileptic agents having fewer or no side effects and have not been suggested as being useful in their own right for other therapeutic purposes.

Despite continued efforts to identify compounds useful for treating neurodegenerative and proliferative disorders there is still a great need for useful compounds of increased efficacy and potency.

SUMMARY OF THE INVENTION

This invention provides compounds, pharmaceutical compositions and methods useful for promoting neuronal function and inhibiting cell mitosis. Accordingly, this invention also provides methods of preventing and treating neurodegenerative and proliferative disorders.

The compounds of this invention have the general formula (I)

(I)

wherein
R$^1$ is —C≡CH, —CH=CH$_2$ or —CH$_2$—CH$_3$,
R$^2$ is a saturated, unsaturated, branched or unbranched C$_1$–C$_{30}$ alkyl group which is optionally substituted with a C$_3$–C$_9$ aliphatic or aromatic cyclohydrocarbon or heterocyclic group.
M is a hydrogen or a metal atom. Formula I is not 2-n-propyl-4-pentynoic acid (4-yn-VPA) or 2-n-propyl-4-pentenoic acid (4-en-VPA) and when R$^1$ is —CH$_2$—CH$_3$, R$^2$ is C$_5$ to C$_{30}$.

This invention also provides a method of making the compounds of the invention.

This invention also provides pharmaceutical compositions useful for inhibiting cell mitosis and/or promoting neuronal function comprising effective amounts of the compounds suitable for use in the treatments of the invention with a pharmaceutical carrier suitable for administration to an individual.

In addition, this invention relates to methods of promoting neuronal function and/or survival, and in particular to methods of treating individuals with neurodegenerative disorders. The compounds useful for treating neurodegenerative disorders include those of formula I as described above including 2-n-propyl-4-pentenoic acid and 2-n-propyl-4-pentynoic acid, as well as those of formula II (II)

wherein
R$^3$ and R$^4$ are independently of one another C$_1$–C$_{30}$ saturated or unsaturated, branched and/or unbranched aliphatic hydrocarbon, optionally substituted by a C$_{3-9}$ aliphatic or aromatic cyclohydrocarbon, or heterocyclic group.
M is hydrogen or a metal atom.

The compounds and compositions of this invention which are neurotrophic may be used to promote the survival and function of neurons which would otherwise have diminished function, degenerate or die. Accordingly, in addition to treating individuals diagnosed with a neurodegenerative disorder, the compounds and compositions of this invention may also be used prophylactically to prevent or retard the onset of neurodegenerative disorders in individuals identified as being at risk for developing such disorders.

In another embodiment of this invention, the compounds and compositions useful for treating neurodegenerative disorders may also be used to treat proliferative disorders. The antiproliferative activity of the compounds and compositions may be used to prevent or retard the formation of a wide variety of tumors by administering the compounds and compositions to a person in need of treatment. This treatment is especially useful for treating tumors of neuronal or glial origin given that these compounds penetrate the CNS.

It is an object to this invention to provide neurotrophic compounds useful for enhancing the survival of neurons and glial cells.

It is another object of this invention to provide compounds and compositions useful for promoting the expression of characteristics associated with mature functioning neuronal or glial cells.

By promoting the survival and function of neuronal or glial cells, it is an object of this invention to provide compounds and compositions useful for the prevention and/or treatment of a variety of neurodegenerative disorders.

Another object of this invention is to provide compounds and compositions useful for inhibiting the pathologic proliferation of neuronal, glial or related cells.

DETAILED DESCRIPTION OF THE INVENTION

This invention relates to derivatives of valproic acid, methods of their preparation and pharmaceutical compositions comprising these compounds. This invention also relates to a method of promoting neuronal function and differentiation which is useful for preventing and treating neurodegenerative disorders. The anti-mitotic activity of the compounds and compositions of the invention are useful for arresting cells in a specific stage of the cell cycle and for the prevention and treatment of neoplastic disease.

The objects of this invention are accomplished by providing potent teratogenic analogs of valproic acid which penetrate the CNS as neurotrophic/neuroprotective agents capable of treating and retarding the onset of neurodegenerative diseases. The compounds and compositions of this invention are also useful for controlling the cell proliferative rate and the metastatic potential of neoplastic or potentially neoplastic cells.

Accordingly, the compounds of this invention have the general formula (I)

(I)

wherein $R^1$ is —C≡CH, —CH=CH$_2$, or —CH$_2$—CH$_3$, $R_2$ is independently a saturated, unsaturated with at least one double or triple bond, branched or unbranched C$_{1-30}$ alkyl group, optionally substituted with an aliphatic or aromatic C$_{3-9}$ cyclohydrocarbon or heterocyclic group;

with the proviso that when $R^1$ is CH$_2$—CH$_3$, $R^2$ is C$_{5-30}$, and that formula I is not 2-n-propyl-4-pentynoic acid or 2-n-propyl-4-pentenoic acid (4-en-VPA).

M is a hydrogen or a metal atom.

This invention also includes the racemic mixtures and the separate enantiomeric R and S forms of the compounds and pharmaceutical acceptable salts thereof.

Preferably, $R^1$ is —C≡CH and $R^2$ is an unbranched saturated $C_2$—$C_{10}$ alkyl group. More preferred, $R^2$ is an unbranched, saturated $C_4$—$C_6$ alkyl group. Examples of preferred substituents for $R^2$ include —$(CH_2)_{1-9}$—$CH_3$, more preferred is —$(CH_2)_{3-6}$—$CH_3$, and most preferred is —$(CH_2)_{4-5}$—$CH_3$. Most preferred compounds are 2-n-butyl-4-pentynoic acid ($R^1$=—C≡H; $R^2$=—$(CH_2)_3$—$CH_3$)), 2-n-pentyl-4-pentynoic acid ($R^1$=—C≡H; $R^2$=—$(CH_2)_4$—$CH_3$) and 2-n-hexyl-4-pentynoic acid ($R^1$=—C≡H; $R^2$=—$(CH_2)_5$—$CH_3$). In addition, although both enantioners and their racemic mixtures are considered within the scope of this invention, the S-enantiomeric form is preferred. Preferred metal atoms are sodium or other alkali metals, as well as alkaline earth metals such as, for example, calcium or magnesium.

The teratogenic, antiproliferative and prodifferentiative potencies of the preferred compounds are much higher than of the antiepileptic drug valproic acid.

Further branching of $R^1$ or $R^2$ reduces the potency of the corresponding compounds. This is demonstrated by the low teratogenic, antiproliferative and prodifferentiative potency of the following compound.

(III)

Unsaturation between $C_2$ and $C_3$ (IV) as well as methylation of the $C_5$ (V, VI) also lowers, but does not abolish, the above mentioned cellular neurotrophic and antiproliferative activity 2-n-propyl-2-pentenoic acid (IV)

2-n-propyl-4-hexenoic acid (V)

2n-propyl-4-hexynoic acid (VI)

In agreement with our basic hypothesis, compound IV (Nau et al., *Neurology* (1984) 34:400–402; Nau and Loscher, *Fundam Appl. Toxicol.* (1986) 6:669–676; Nau and Scott, *Nature* (1986) 323:276–278; Vorhees et al., *Teratology* (1991) 43:583–590; Ehlers et al., *Devel. Pharmacol. Ther.* (1992) 19:196–204 and VI (Nau et al., *Phamacol. & Toxicol.* (1991) 69:310–321; Elmazar et al., *J. Pharm. Sci.* (1993) 82:1255–1258 has very low or undetectable teratogenic activities, but good anticonvulsant properties in experimental models.

The compounds and compositions of this invention are more potent teratogenic analogues of valproate and exhibit greater antiproliferative and neurotrophic/neuroprotective activity than the parent. In contrast to saturated valproate analogues (where both chains must contain 3 carbon atoms each for maximal activity) a double or triple bond in the c position of one chain exhibits higher activities when the other chain contains 4 to 10 carbon atoms. The 2-n-propyl-4-pentynoic acid, 2-n-butyl-4-pentynoic acid, 2-n-pentyl-4-pentynoic acid, 2-n-hexyl-4-pentynoic acid, 2-n-hepta-4-pentynoic acid and 2-n-octa-4-pentynoic acid are the most potent valproate-related teratogens synthesized. 2-n-butyl-4-pentynoic acid, 2-n-pentyl-4-pentynoic, 2-n-hexyl-4-pentynoic acid, 2-n-hepta-4-pentynoic acid and 2-n-octa-4-pentynoic acid are more preferred. Most preferred are 2-n-pentyl-4-pentynoic acid and 2-n-hexyl-4-pentynoic acid.

The preferred compounds for use with this invention possess a chiral alpha-carbon. As a result of chirality, the efficacy and potency of different enantiomeric forms may differ. For example, S-2-n-propyl-4-pentynoic acid has significantly greater teratogenic potential than the R-enantiomeric form. Hauck and Nau, *Pharm. Res.* (1992) 9:850–855; Hauck et al. *Toxicol. Lett.* (1992) 60:145–153. See Nau et al. *Pharmacol. Toxicology* (1991) 69:310–321 which is incorporated herein by reference. Although there is no general rule of the above-identified compounds, the S enantioneric form is preferred.

The compounds of this invention are prepared by reacting an appropriately substituted malonic acid diethylester with an appropriate unsaturated alkylating agent such as a straight-chain alkylhalide. The product is then hydrolyzed and decarboxylated.

This reaction can also be carried out in the reciprocal manner in that a malonic acid diethylester, substituted with an unsaturated function is reacted with an appropriate alkylhalide. This reaction is again followed by hydrolysis and decarboxylation.

The novel compounds of this invention may be produced according to the method of this invention. In one embodiment, the method of synthesizing the compounds comprises combining a malonic acid diester reactant with a first halide reactant having the general formula $R^2$—X (VII)

wherein $R^2$ is a saturated or unsaturated branched or unbranched $C_1$—$C_{30}$ alkyl group and X is a halide. This first reaction produces a 2-alkyl-malonic acid diester. The 2-alkyl-malonic acid diester is then further combined with a second halide reactant having the general formula $R^1$—$CH_2$—X (VIII)

wherein $R^1$ is —C≡CH, —CH=$CH_2$ or —$CH_2$—$CH_3$ to produce compounds with the general formula

(IX)

wherein $R^5$ is an alkyl group.

The resulting diesters are then hydrolyzed, decarboxylated and optionally converted into a salt.

In an alternative embodiment, the order of carrying out the reactions is reversed, such that the $R^1$—$CH_2$—X is combined with the malonic acid diester followed by further reaction with the $R^2$—X.

In a preferred method of preparing the compounds of this invention, malonic acid diethylester is treated with a base, for example, sodium ethylate, to deprotonate carbon 2. Subsequent treatment of the resulting deprotonated ester with an alkylating agent in the form of a straight-chain alkyl halide yields a 2-n-alkyl-malonic acid diethylester.

(X)

This product is further alkylated with sodium ethylate and either 2-propynehalide to yield XI

(XI)

or 2-propenehalide to yield XII (XII)

or 2-propylhalide to yield XIII (XIII)

The diesters (XI) and (XII) and (XIII) are hydrolyzed and decarboxylated with potassium hydroxide in ethanol/water with heat treatment.

Another embodiment of this invention is the promotion of neural function by contacting neural cells with a neurotrophic amount of a compound of formula (II)

(II)

wherein $R^3$ and $R^4$ are independently of each other saturated or unsaturated, branched, or unbranched, $C_1$–$C_{30}$ aliphatic hydrocarbons, optionally possessing at least one double or triple bond. Preferably $R^3$ and $R^4$ are unbranched, and $R^3$ is less than or equal to a three carbon chain. $R^4$ preferably is a saturated alkyl group and is preferably from $C_2$–$C_{10}$, as in for example —$(CH_2)_{1-9}$—$CH_3$, and more preferably from $C_4$ to $C_6$, as in for example —$(CH_2)_{3-5}$—$CH_3$. In addition to the compounds stated above in connection with formula I, other compounds which are useful for the promotion of neuronal function and inhibition of cell mitosis are described in Nau et al. PCT application PCT/DE93/00861 published as WO94/06743, and which is incorporated herein by reference.

Preferred compounds useful for promoting neuronal function include for example, 2-n-propyl-4-pentynoic acid ($R^3$=—$CH_2$—C≡CH; $R^4$=—$(CH_2)_2$—$CH_3$); valproic acid ($R^3$=$R^4$=—$(CH_2)_2$—$CH_3$); 2-n-propylhexanoic acid ($R^3$=—$(CH_2)_3$—$CH_3$, $R^4$=—$(CH_2)_2$—$CH_3$); and 2-n-butylhexanoic acid ($R^3$=$R^4$=—$(CH_2)_3$—$CH_3$).

The promotion of neuronal function is particularly useful for preventing and treating neurodegenerative disorders. Neurodegenerative disorders include any disorder resulting in neuronal degeneration which is responsive to at least one of the valproate analogues or valproate itself.

The neurotrophic activity associated with valproate and its analogues may be determined based on in vitro indices of differentiation, including inhibition of mitosis, increase in neurite outgrowth, and NCAM expression. For example, the ability to promote neurite outgrowth is correlated with enhanced survival of certain cultured neural cells including embryonic sensory and sympathetic neurons. Proliferating immature neuroblasts, in vitro, have a rounded shape and are loosely adherent to culture surfaces. In the presence of a neurotrophic factor, these cells become more adherent and sprout processes known in the art as neurites.

Accordingly, in vitro neurite outgrowth may be used as an assay for determining concentrations of compound in contact with target cells which would be expected to achieve desirable neuroprotecting effects.

Methods of assessing neurite outgrowth in vitro are well known in the art and, for example, may be assessed through direct microscopic visual inspection or through the use of computer aided image processing.

Another characteristic of neurotrophic factors which may be used to assess the neuroprotective action of the compounds and compositions of this invention is their ability to promote survival of certain specific cell types. For example, NGF is required in vitro for the survival of certain specific cell types which die in the absence of NGF. Such NGF dependent cells include neurons of the chick dorsal rat ganglia at about embryonic day E5 to E8.

Scanning electron microscopy illustrates the cells ability to increase cell-substratum adhesivity. They eliminate rounded and clustered growth, typical of tumor cells, and induce a flattening and greater interaction with the substratum (FIG. 2). In vivo, it is generally believed that these neurites further differentiate into axons and dendrites and form synapses with other neurons. During diseases involving neurodegeneration, there may be a loss of synapses and degeneration of axons and dendrites resulting in a deficit of neuronal function.

Another index of differentiation resulting from the neurotrophic activity of valproate analogues is an increase in NCAM expression. Further, increases in NCAM prevalence enhances neurite outgrowth. Doherty et al., *Nature* (1990) 343:464–466. NCAM has been reported as playing a fundamental role in memory formation as intraventricular infusion of anti-NCAM during consolidation of a recent learning event induces an amnesia. Doyle et al., *J. Neurochem.* (1992) 59:1570–1573, which is incorporated herein by reference. Rapid endocytosis of the Aplysia NCAM homologue was reported following a serotonin-induced change in synapse structure in vitro. Bailey et al., *Science* (1992) 256:645–649.

During development of individual brain regions, or in adults exhibiting ongoing neurogenesis, NCAM transiently increases its sialylation state. See review, Regan, *Int. J. Biochem.* (1991) 23:513–523, which is incorporated herein by reference, Rougon (1993) *Eur. J. Cell Biol.* 61:197–207. The synapse specific NCAM isoform (NCAM 180) which is associated with differentiated neurons increases its sialylation state during later stages of development until the period of synaptogenesis is complete. Breen et al., *J. Neurochem* (1988) 50:712–716. A similar isoform-specific sialylation of NCAM 180 occurs during consolidation of a passive-avoidance response. Doyle et al., *J. Neurosci Res.*, (1992) 31:513–523.

We have observed the ability of these compounds and compositions to exert an in vivo neurotrophic action in acute and chronic studies employing adult male Wistar rats. The acute studies determined their ability to reverse the amnesic effect of a 6 hour post-training scopolamine lesion in a one trial passive avoidance paradigm as has been employed for other neuroprotective agents (Doyle et al., J. Neurochem. 1993 61: 266–272; Doyle and Regan, J. Neural Transm. 1993 92: 33–49).

Accordingly, the methods of treatment and prevention of neurodegenerative diseases rely on the ability of valproate and its analogues to possess neurotrophic activity such as promoting neurite outgrowth and survival of neuronal cells and NCAM expression.

It is contemplated that the methods of treatment may provide benefits to persons with neurodegeneration from disorders including, but not limited to ALS, Alzheimers disease, Parkinson's disease, Huntington's disease, diabetic neuropathy and stroke. In addition, the neurite promoting activity of the disclosed compounds and compositions would also provide benefits to individuals with traumatic nerve injury.

In another embodiment of this invention, methods are provided for arresting cells in a specific stage of the cell cycle which leaves the cells in a differentiated state by contacting cells with a mitotic inhibitory amount of a compound of formula II as described above. Preferred substituents for $R^3$, $R^4$ and M for inhibiting mitosis are the same as those for promoting neuronal function, with the proviso that formula II is not valproate if simply used to inhibit cell mitosis. Preventing mitosis in this manner is useful for enhancing the expression of specific proteins associated with the differentiated phenotype. This enhanced expression facilitates purification of such proteins. In addition, arresting or retarding mitosis is useful for treating proliferative disorders by administering to individuals in need of treatment valproate and/or another of its anti-mitotic analogues.

We have observed sensitivity to valproate or its anti-mitotic analogues in all cells tested. Such cell types include: primary astrocytes, human astrocytoma, and those from cardiac, renal, and immune systems. Accordingly, the anti-proliferative action of valproate and its other analogues described herein should have broad applicability for a wide variety of tumors derived from a variety of cell types and particularly those mentioned above.

The neurotrophic and/or anti-mitotic effective amounts of valproate and active analogues may be determined using standard dose-response curves. Accordingly, representative cells may be cultured in vitro in the presence of varying concentration of test compound. At an appropriate time, the cells under the different conditions are examined for the appropriate parameter (for example, cell number for anti-mitotic activity; neurite outgrowth for neurotrophic activity) and the $ED_{50}$ may be determined.

Figure 1:
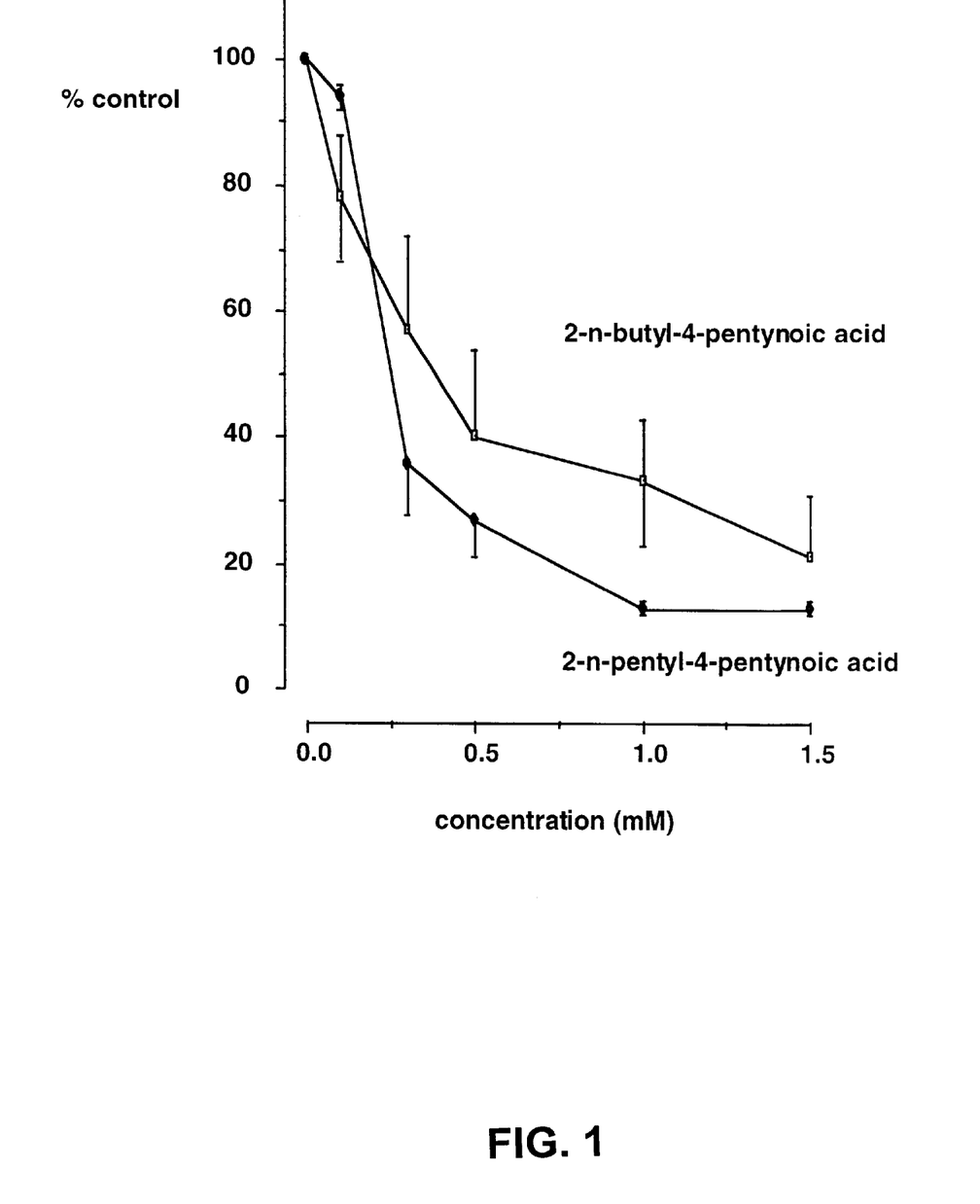
FIG. 1: Dose-Response relationship of antiproliferative effect of 2-n-butyl-4-pentynoic acid; and 2-n-pentyl-4-pentynoic acid. Neuro-2a neuroblastoma cells were cultured in 25 cm$^2$ flasks for 48 hours in the presence of test medium. After 48 hours, cells were observed, photographed and harvested with trypsin for counting using a haemocytometer. Cell number is expressed as percentage mean ±SEM (n=3) of control values.
Figure 2A:
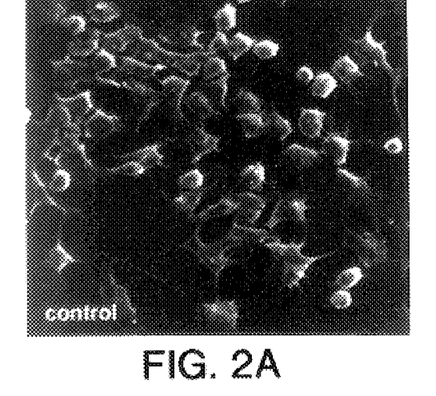
FIGS. 2A–2E: Induction of neurite outgrowth of neuro-2a neuroblastoma cells. Neuroblastoma cells were cultured in the presence of 2-n-butyl-4-pentynoic acid (1.0 mM, 2 mM); and 2-n-pentyl-4-pentynoic acid (0.3 mM, 0.5 mM). Test medium was added to cells after 24 hours in culture and maintained as a test medium for 48 hours after which they were fixed in 2.5% glutaraldehyde and 0.5M sodium phosphate buffer overnight at 4° C. Cells were postfixed with osmium tetroxide and prepared for scanning microscopy as described. Fixed and stained cells were observed in a scanning electron microscope at an accelerating voltage of 15 kV.
Figure 2B:
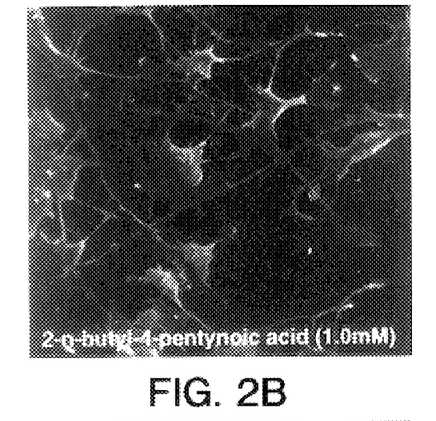
Figure 2C:
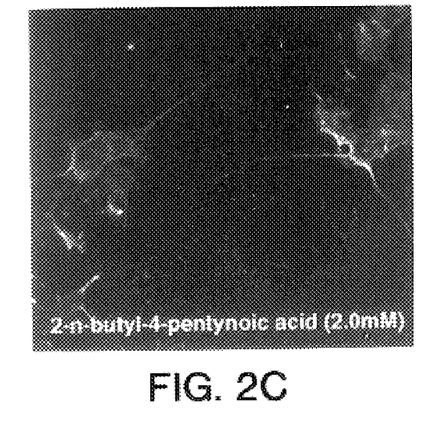
Figure 2D:
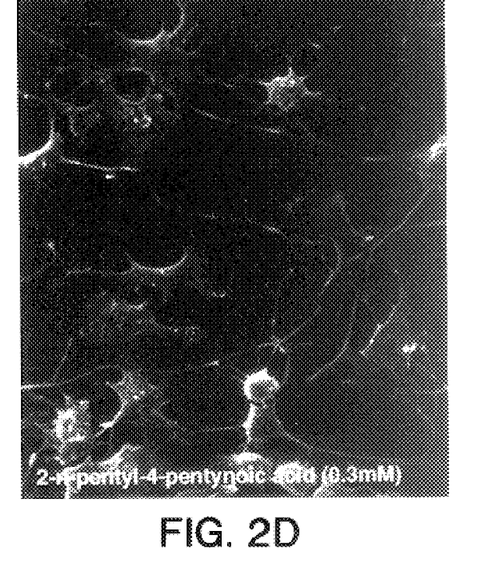
Figure 2E:
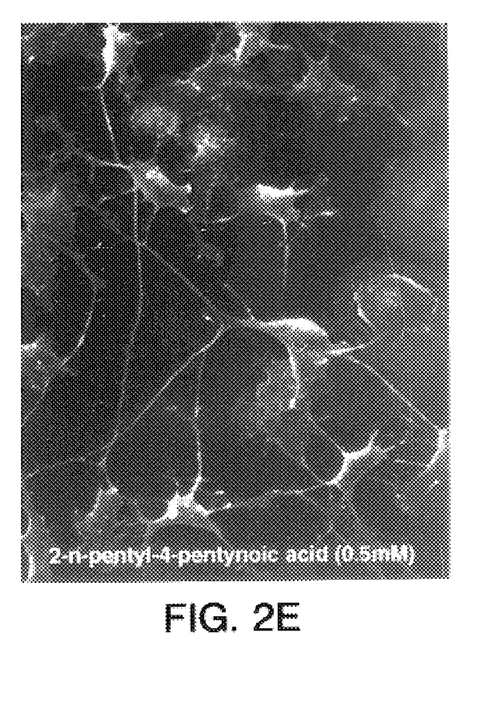

The preferred compounds of this invention exert a most profound antiproliferative action with ED50 values well below (<0.5 mM) those observed with valproate (FIG. 1). Thus, these compounds may be expected to act at concentrations which will be devoid of the sedative and hepatotoxic side effects of valproate. The preferred compounds also exert the prodifferentiative action observed with valproate.

In the neuro-2a neuroblastoma cell line they induce a marked neuritogenic response which correlates with their antiproliferative potential (FIG. 2).

Figure 3A:
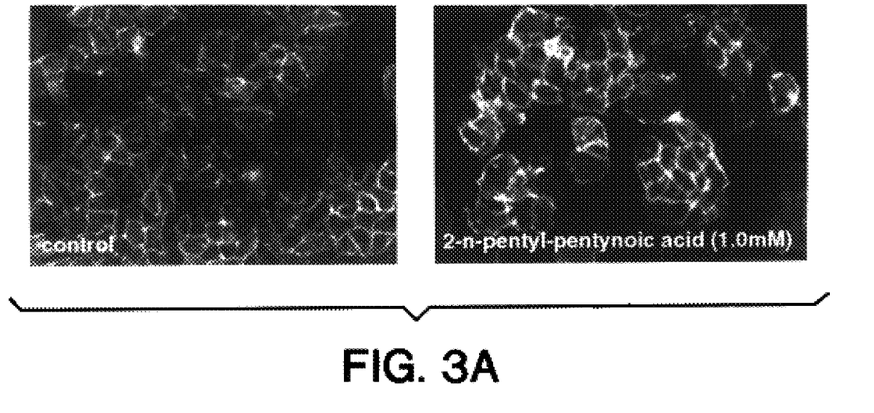
FIGS. 3A–3B: Neural Cell Adhesion Molecule (NCAM) immunofluorescence in neuro-2a neuroblastoma cells. Panel A. Cells grown in the presences of 2-n-pentyl-pentynoic acid (1.0 mm) show increased immunofluorescence directed against NCAM compared to control cells. Panel B. Neuroblastoma cells were cultured for 48 hours in the presence of increasing concentrations of 2-n-butyl-4-pentynoic acid and 2-n-pentyl-4-pentynoic acid. They were then fixed and prepared for staining with rabbit anti-NCAM antibody. A second anti-rabbit antibody conjugated to rhodamine was incubated with the cells to detect bound anti-NCAM antibody. Cells were observed with a fluorescence microscope at an excitation wavelength of 535 nm. Immunofluorescence is expressed as mean ±SEM.
Figure 3B:
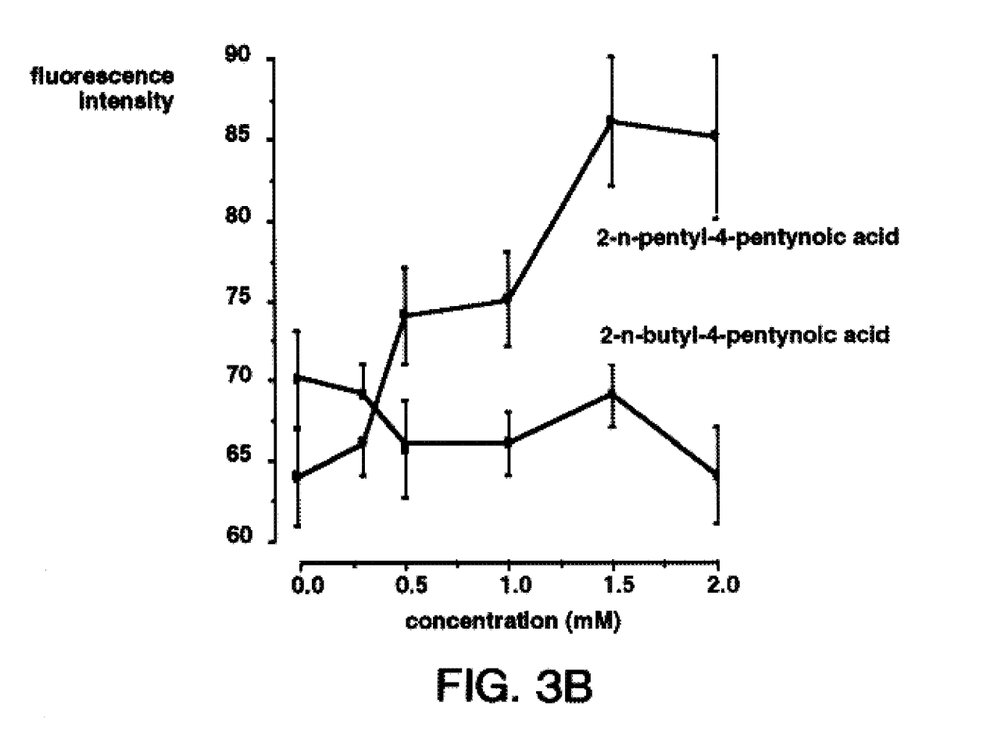

In addition, the more potent of these compounds increase neural cell adhesion molecule (NCAM) prevalence (FIG. 3). This cell recognition system regulates neural plasticity during development and, later, during information storage in the adult animal by altering its prevalence and glycosylation state (Doyle et al., *J. Neurosci Res.*, (1992) 31:513–523). Drugs which reverse scopolamine-induced amnesia, such as piracetam-related compounds, appear to act through a neuroprotective mechanism which involves a non-specific increase in NCAM glycosylation and/or prevalence (Doyle et al., *J. Neurochem.* (1993) 61:266–272). Consequently agents which would induce NCAM expression may be predicted to have neuroprotective potential.

This invention also provides pharmaceutical compositions useful for treating neurodegenerative or proliferative disorders comprising a compound selected from formulas I or II as described above. In addition to the compounds of formula I or II, the pharmaceutical composition may also comprise adjuvant substances and carriers. The compositions may be in the form of tablets, capsules, powders, granules, lozenges, suppositories, reconstitutable powders, or liquid preparations such as oral or sterile parenteral solutions or suspensions.

In order to obtain consistency or administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers, for example lactose, sugar, maize-starch, calcium phosphate, sorbitol or glycine; disintegrants, for example starch, polyvinylpyrrolidone, sodium starch glycolate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead or being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The dose of the compound used in the treatment of such disease will vary in the usual way with the seriousness of the disorders, the weight of the sufferer, and the relative efficacy of the compound.

Antiproliferative and neuroprotective actions should be sufficient to achieve the desired inhibition of mitosis or neuroprotection without serious hetaptotoxic side effects. The plasma concentrations to be achieved will be sufficient to provide therapeutically effective concentrations of compound in contact with the target cells. Standard clinical techniques may be used to determine the effective amount of compound to be administered to achieve the desired therapeutic effect. Dose response curves may be determined first in vitro in a relevant animal model to determine ranges of expected therapeutic concentrations in humans. For example, mitosis of mouse neuro-2a-neuroblastoma cells is inhibited by valproate with an $ED_{50}$ of 1.0–1.3 mM. Other cell lines, including those of human origin may be used to assesses activity as well.

EXAMPLE 1

0.1 mol n-butyl malonic acid diethylester and 0.1 mol 3-bromo-1-propine were placed in a dry argon flushed flask and heated to 60° C. To this mixture was added 0.1 mol sodium ethanolat (prepared from 0.1 mol sodium and 50 mol dry ethanol) dropwise such as to keep the mixture boiling. After completion of the addition, the mixture was heated until TLC (Silica alu sheets, hexane/ethylacetate 7.5/1) showed absence of starting material (usually 1–2 hours). The ethanol was evaporated under reduced pressure, the remaining salts were dissolved in water and the product was extracted three times with $CH_2Cl_2$. The organic phase was dried over sodium sulfate and evaporated. The distillation under reduced pressure resulted in the unsymmetrically substituted malonic acid diethylester.

$bp_{0.3\ mbar}$: 78–82° C.

The dialkylated malonic esters were heated in a solution of 20.3 g (0.35 mol) potassium hydroxide, 50 ml water and 100 ml ethanol. After completion of the saponification, ethanol was evaporated under reduced pressure. The remaining residue was diluted with water and washed with ether. The water layer was acidified with concentrated HCl (pH<2) and extracted with ether. Drying over anhydrous sodium sulfate and concentration under reduced pressure yielded crude dialkyl malonic acid. Decarboxylation was achieved by heating of the crude product (120–180° C.). The dark residue was distilled twice in vacuo resulted in the desired products.

Overall yield: 18%;

$bp_{0.1\ mbar}$: 75–78° C.; $1_{H\text{-}NMR}$ (CDCl$_3$): 0.94 (3H, t, CH$_3$), 1.34 (4H, m, 2×CH$_2$), 1.72 (2H, m, CH$_2$—CHRCOOH), 2.04 (1H, t, C≡C—H), 2.36–2.68 (3H, m, CHRCOOH—CH$_2$—C≡C), 11.88 (1H, s, broad, COOH).

EXAMPLE 2

0.1 mol n-pentyl malonic acid diethylester is reacted with 0.1 mol 3-bromo-1-propine as described in example 1.

Overall yield: 14%; $bp_{15\ mbar}$: 135° C.; $1_{H\text{-}NMR}$ (CDCL$_3$): 0.92 (3H, t, CH$_3$), 1.32 (6H, m, 3×CH$_2$), 1.72 (2H, m, CH$_2$—CHRCOOH), 2.04 (1H, t, C≡C—H), 2.40–2.72 (3H, m, CHRCOOH-CH$_2$—C≡C), 11.32 (1H, s, broad, COOH).

EXAMPLE 3

(+)-2-(2-propinyl)-Octanoic acid (Hexyl-4-yn)

Synthesis is by the Dianion Method (Petragnani, Synthesis 521, 1982).

All glassware was oven dried and the reaction apparatus was flushed with argon throughout the entire operation.

Lithium-dianion (0.2 Mol) was prepared by adding 0.2 Mol n-butyl-lithium to a solution of 0.2 Mol freshly distilled diisopropylamine and 130 ml dry tetrahydrofurane at 0° C. Octanoic acid (0.1 Mol) was added followed by 19 hexamethylphosphoric acid triamide to effect solution of the dianion. The resulting mixture was stirred at room temperature for 30 min followed by cooling to −60° C. and addition of 3-bromo-1-propin (0.1 Mol) quickly via a syringe. The temperature rose instantly. After cooling back to −60° C., the reaction was stirred and monitored by TLC (Hexane: Ethylacetate=7.5:1 plus 5 % acetic acid) until completion (ca 1.5 h). Cooling was removed and 200 ml 10% HCl was added. The phases were separated and the water phase was extracted twice with ether. The combined organic phases were washed with half saturated NaCl solution and dried with Na$_2$SO$_4$. Evaporation of the solvent yielded a yellow oil. Destillation yielded a colorless liquid (bp. 82–84° C., 0.1 mbar).

$^1$H NMR (CDCl$_3$)=0.88 (3H, t, CH$_3$), 1.40 (8H, mc, CH$_2$), 1.90 (2H, mc, CH$_2$) 2.04 (1H, t, ≡—H), 2.32–2.68 (3H, m, CH$_2$, H$_\alpha$), 12.04 (1H, s broad, COOH).

EXAMPLE 4

The following non-limiting preferred examples are compounds within the scope of this invention:

2-n-propyl-4-pentynoic acid
2-n-prop-1$^1$-enyl-4-pentynoic acid
2-n-prop-2$^1$-enyl-4-pentynoic acid
2-i-propyl-4-pentynoic acid
2-i-propenyl-4-pentynoic acid
2-n-butyl-4-pentynoic acid
2-n-butyl-4-enyl-4-pentynoic acid
2-n-but-2$^1$-enyl-4-pentynoic acid
2-n-but-3$^1$-enyl-4-pentynoic acid
2-(1$^1$-methylbutyl)-4-pentynoic acid
2-(1$^1$-methylprop-1$^1$-enyl)-4-pentynoic acid
2-(1$^1$-methylprop-2$^1$-enyl)-4-pentynoic acid
2-(2$^1$-methylpropyl)-4-pentynoic acid
2-(2$^1$-methylprop-1$^1$-enyl)-4-pentynoic acid
2-(2$^1$-methylprop-2$^1$-enyl)-4-pentynoic acid
2-tert.-butyl-4-pentynoic acid
2-n-pentyl-4-pentynoic acid
2-(1$^1$-methylbutyl)-4-pentynoic acid
2-(2$^1$-methylbutyl)-4-pentynoic acid
2-(3$^1$-methylbutyl)-4-pentynoic acid 2-($1^1,1^1$-dimethylpropyl)-4-pentynoic acid
2-($1^1,2^1$-dimethylpropyl)-4-pentynoic acid
2-($2^1,2^1$-dimethylpropyl)-4-pentynoic acid
2-n-hexyl-4-pentynoic acid
2-n-hex-$1^1$-enyl-4-pentynoic acid
2-n-hex-$2^1$-enyl-4-pentynoic acid
2-n-hex-$3^1$-enyl-4-pentynoic acid
2-n-hex-$4^1$-enyl-4-pentynoic acid
2-n-hex-$5^1$-enyl-4-pentynoic acid
2-($1^1$-methylpentyl)-4-pentynoic acid
2-($1^1$-methylpent-$1^1$-enyl)-4-pentynoic acid
2-($1^1$-methylpent-$2^1$-enyl)-4-pentynoic acid
2-($1^1$-methylpent-$3^3$-enyl)-4-pentynoic acid
2-($1^1$-methylpent-$4^1$-enyl)-4-pentynoic acid
2-($2^1$-methylpentyl)-4-pentynoic acid
2-($2^1$-methylpent-$1^1$-enyl)-4-pentynoic acid
2-($2^1$-methylpent-$2^1$-enyl)-4-pentynoic acid
2-($2^1$-methylpent-$3^1$-enyl)-4-pentynoic acid
2-($2^1$-methylpent-$4^1$-enyl)-4-pentynoic acid
2-($3^1$-methylpentyl)-4-pentynoic acid
2-($3^1$-methylpent-$1^1$-enyl)-4-pentynoic acid
2-($3^1$-methylpent-$2^1$-enyl)-4-pentynoic acid
2-($3^1$-methylpent-$3^1$-enyl)-4-pentynoic acid
2-($3^1$-methylpent-$4^1$-enyl)-4-pentynoic acid
2-($4^1$-methylpentyl)-4-pentynoic acid
2-($4^1$-methylpent-$1^1$-enyl)-4-pentynoic acid
2-($4^1$-methylpent-$2^1$-enyl)-4-pentynoic acid
2-($4^1$-methylpent-$3^1$-enyl)-4-pentynoic acid
2-($4^1$-methylpent-$4^1$-enyl)-4-pentynoic acid
2-($1^1,1^1$-dimethylbutyl)-4-pentynoic acid
2-($1^1,1^1$-dimethylbut-$2^1$-enyl)-4-pentynoic acid
2-($1^1,1^1$-dimethylbut-$3^1$-enyl)-4-pentynoic acid
2-($1^1,2^1$-dimethylbutyl)-4-pentynoic acid
2-($1^1,2^1$-dimethylbut-$1^1$-enyl)-4-pentynoic acid
2-($1^1,2^1$,dimethylbut-$2^1$-enyl)-4-pentynoic acid
2-($1^1,2^1$,dimethylbut-$3^1$-enyl)-4-pentynoic acid
2-($1^1,3^1$-dimethylbutyl)-4-pentynoic acid
2-($1^1,3^1$-dimethylbut-$1^1$-enyl)-4-pentynoic acid
2-($1^1,3^1$-dimethylbut-$2^1$-enyl)-4-pentynoic acid
2-($1^1,3^1$-dimethylbut-$3^1$-enyl)-4-pentynoic acid
2-($2^1,2^1$-dimethylbutyl)-4-pentynoic acid
2-($2^1,2^1$-dimethylbut-$3^1$-enyl)-4-pentynoic acid
2-($2^1,3^1$-dimethylbutyl)-4-pentynoic acid
2-($2^1,3^1$-dimethylbut-$1^1$-enyl)-4-pentynoic acid
2-($2^1,3^1$-dimethylbut-$2^1$-enyl)-4-pentynoic acid
2-($2^1,3^1$-dimethylbut-$3^1$-enyl)-4-pentynoic acid
2-($3^1,3^1$-dimethylbutyl)-4-pentynoic acid
2-($3^1,3^1$-dimethylbut-$1^1$-enyl)-4-pentynoic acid
2-($1^1,1^1,2^1$-trimethylpropyl)-4-pentynoic acid
2-($1^1,1^1,2^1$-trimethylprop-2-enyl)-4-pentynoic acid
2-($1^1,2^1,2^1$-trimethylpropyl)-4-pentynoic acid
2-n-heptyl-4-pentynoic acid
2-($1^1$-methylhexyl)-4-pentynoic acid
2-($2^1$-methylhexyl)-4-pentynoic acid
2-($3^1$-methylhexyl)-4-pentynoic acid
2-($4^1$-methylhexyl)-4-pentynoic acid
2-($5^1$-methylhexyl)-4-pentynoic acid
2-($1^1,1^1$-dimethylpentyl)-4-pentynoic acid
2-($1^1,2^1$-dimethylpentyl)-4-pentynoic acid
2-($1^1,3^1$-dimethylpentyl)-4-pentynoic acid
2-($1^1,4^1$-dimethylpentyl)-4-pentynoic acid
2-($2^1,2^1$-dimethylpentyl)-4-pentynoic acid
2-($2^1,3^1$-dimethylpentyl)-4-pentynoic acid
2-($2^1,4^1$-dimethylpentyl)-4-pentynoic acid
2-($3^1,3^1$-dimethylpentyl)-4-pentynoic acid
2-($3^1,4^1$-dimethylpentyl)-4-pentynoic acid
2-($4^1,4^1$-dimethylpentyl)-4-pentynoic acid
2-($1^1,1^1,2^1$-trimethylbutyl)-4-pentynoic acid
2-($1^1,1^1,3^1$-trimethylbutyl)-4-pentynoic acid
2-($1^1,2^1,3^1$-trimethylbutyl)-4-pentynoic acid
2-($2^1,2^1,3^1$-trimethylbutyl)-4-pentynoic acid
2-($2^1,3^1,3^1$-trimethylbutyl)-4-pentynoic acid

EXAMPLE 5

Maintenance of Cell Lines

The mouse neuro-2a neuroblastoma cell line (Klebe and Ruddle, 1969 J. Cell Biol., 43:69A) was cultured in Dulbecco's modified Eagle's medium (DMEM; Flow Laboratories) supplemented with 10% fetal bovine serum (Tissue Culture Services), 200 mM glutamine and 100 $\mu$g/ml of gentamicin or 100 units/ml and 100$\mu$g/ml of penicillin/streptomycin antibiotics (Sigma Chemicals). The cells were maintained in a water-humidified atmosphere of 9% $CO_2$ at 37° C. Cells were passaged using 0.025% trypsin (Gibco) in DMEM, and were seeded at a density of 1×10$^4$ cells/cm$^2$.

Antiproliferative Assay

Neuro-2a cells were seeded in 25 cm$^2$ flasks (Costar) at a density of 1×10$^4$ cells/cm$^2$. Following a recovery period of 24 h, the agent to be examined was added to the cells in a vehicle of dimethyl sulphoxide (DMSO), the volume of which was 0.2% of the total volume of medium bathing the cells. A flask containing the DMSO vehicle alone was employed as control. Following incubation for 48 h, cells were examined using an inverted phase contrast microscope (Leitz Diavert) and photographed (Ilford 50ASA film). Cells were then harvested by trypsinization and were counted using a haemocytometer (improved Neubauer model).

FIG. 1 shows the resultant decrease in cell proliferation.

Scanning Electron Microscopy

Cells which were to be examined by scanning electron microscopy were grown as previously described in 25 cm$^2$ flasks. Following 48 h exposure to the agent, cells were fixed in a solution of 2.5% glutaraldehyde in 0.1M sodium phosphate buffer, pH 7.4, overnight at 4° C. The cells were post-fixed subsequently in phosphate-buffered 1 % osmium tetroxide for 1 h at room temperature, washed and were dehydrated gradually for 1 hour using a series of ethanol concentrations stepwise from 20, 40, 60, 80 to a final concentration 100%.

Sections of the base of the tissue culture flask were removed and were critical point dried to minimize shrinkage and cracking. This was achieved by placing the samples in a Polaron critical point dryer and purging the chamber several times with $CO_2$ to remove all traces of ethanol. After 1h the temperature and pressure were increased to 40° C. and 1200 lbs/in$^2$, respectively, at which stage the critical point for carbon dioxide had been reached and drying was completed.

Specimens were subsequently removed from the chamber, mounted on stubs suitable for scanning electron microscopy using conductive carbon cement (Neubauer) and were sputter coated with gold under vacuum ($5 \times 10^{-2}$ torr) in the presence of argon gas at a current of 20 mA for 3 minutes (Polaron E5100). Following gold-coating, samples were examined in the scanning electron microscope (JEOL 35C) at an accelerating voltage of 15 kV. Images were recorded on film (Kodak Plus-X Pan 120 film) as shown in FIG. 2.

Fluorescence Microscopy

Cells were seeded in 24-well plates at a density of $1 \times 10^4$ cells/cm$^2$. Following a recovery period of 24 h they were exposed for an additional 48 h to the drug under investigation. Cells were progressively fixed by six ten-minute incubations with DMEM containing increasing concentrations of neutral buffered formalin stepwise from 10, 30, 50, 70, 90 to a final concentration of 100%. When fixation was complete, cells were washed three times with phosphate buffered saline pH 7.4 over a 30 minute period. The cells were then incubated with a 1 in 50 dilution of rabbit anti-NCAM antibody, (Pliophys et al. *J. Neuropsychiatr.* 2:413–417, 1990) in phosphate buffered saline containing 1% (W/V) bovine serum albumin for 1 h at RT and washed three times with phosphate buffered saline, pH 7.4 for 30 minutes. Washed cells were then incubated for 1 h at RT with the secondary anti-rabbit antibody diluted 1 in 50 in phosphate buffered saline containing 1% (W/V) bovine serum albumin (Sigma) which was conjugated to rhodamine. The cells were again washed three times with phosphate buffered saline pH 7.4 and were then mounted using Citifluor (Agar Scientific) containing a fluorescence enhancer. Fluorescence of rhodamine was visualized using an excitatory wavelength of 535 nm (Leica filter block N2.1) on a Leitz DMRB fluorescence microscope. Fluorescence intensity was examined at points of cell-cell contact using a Quantimet 500 Image Analysis System. Fluorescence intensity is expressed as grey level at points of cell contact relative to that observed in the control. FIG. 3 shows the increase in NCAM immunofluorescence.

EXAMPLE 6

Acute and Chronic In vivo Studies.

The ability of the compounds and compositions of this invention to exert an in vivo neurotrophic action was investigated in acute and chronic studies employing adult male Wistar rats. The acute studies determined their ability to reverse the amnesic effect of a 6 hour post-training scopolamine lesion in a one trial passive avoidance paradigm as has been employed for other neuroprotective agents (Doyle et al., J. Neurochem. 1993 61:266–272; Doyle and Regan, J. Neural Transm. 1993 92:33–39.

The 2-n-pentyl-4-pentynoic acid was given in the immediate 3 hour post-training period and followed by scopolamine at the 6 hour post-training time. All dosing was via the intraperitoneal route at the indicated post-training times. Additionally, 3 further groups of at least 3 animals were administered 2-n-pentyl-4-pentynoic acid at 3 hours and vehicle at 6 hours to assess and control for any unwanted effects the compound may have in this paradigm. The data is presented as box plots which indicate the median and interquartile ranges and statistical significance was established by the Mann-Whitney U-test for non-parametric data.

Figure 4:
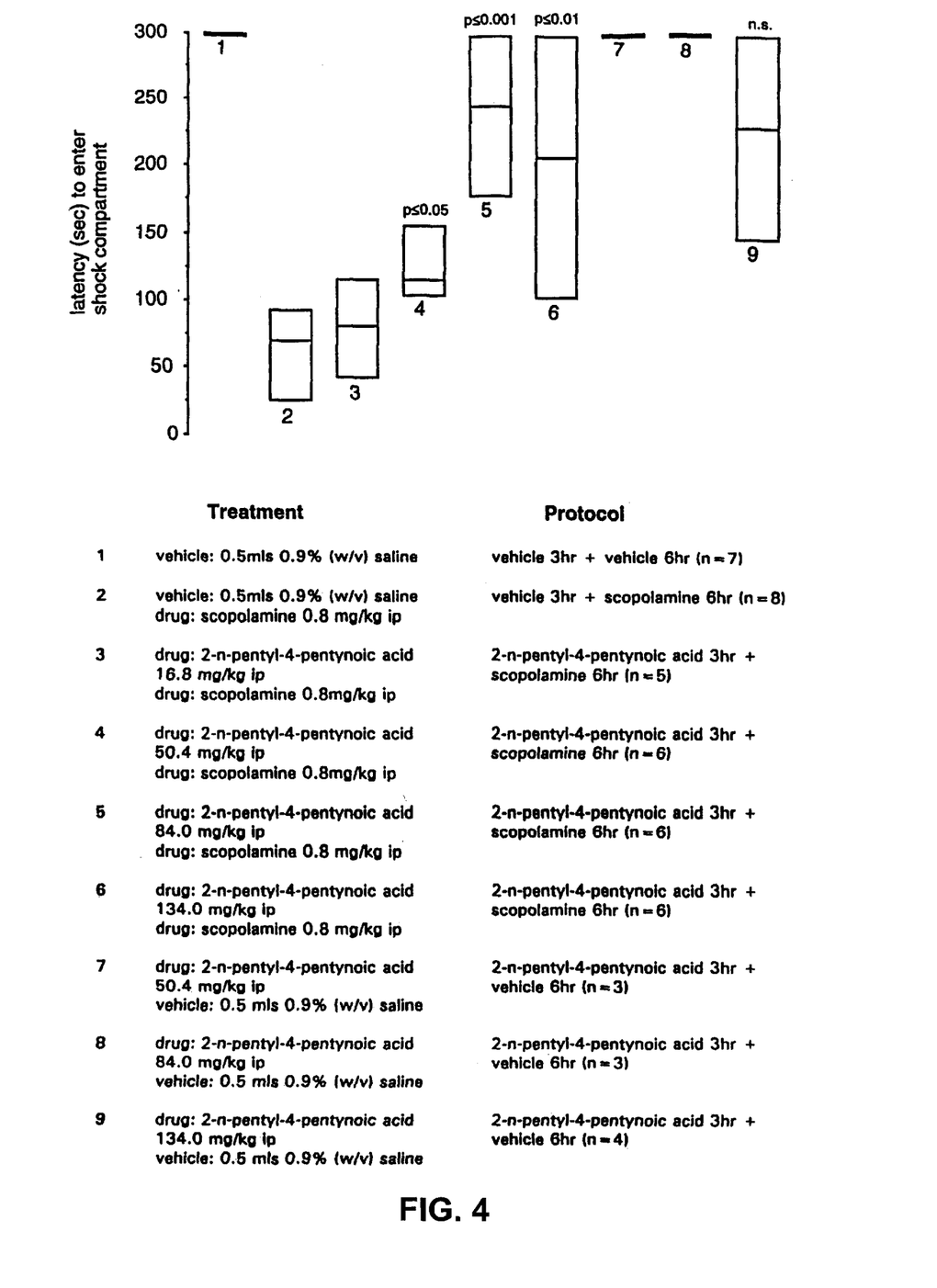
FIG. 4: Dose-dependent reversal of scopolamine-induced amnesia by 2-n-pentyl-4-pentynoic acid. The 2-n-pentyl-4-pentynoic acid and scopolamine were administered at the 3 hour and 6 hour post-training times, respectively, as indicated. The animals were tested for recall at 24 hours and a criterion period of 300 seconds was employed. The results are expressed as median values and interquartile ranges.
Figure 5A:
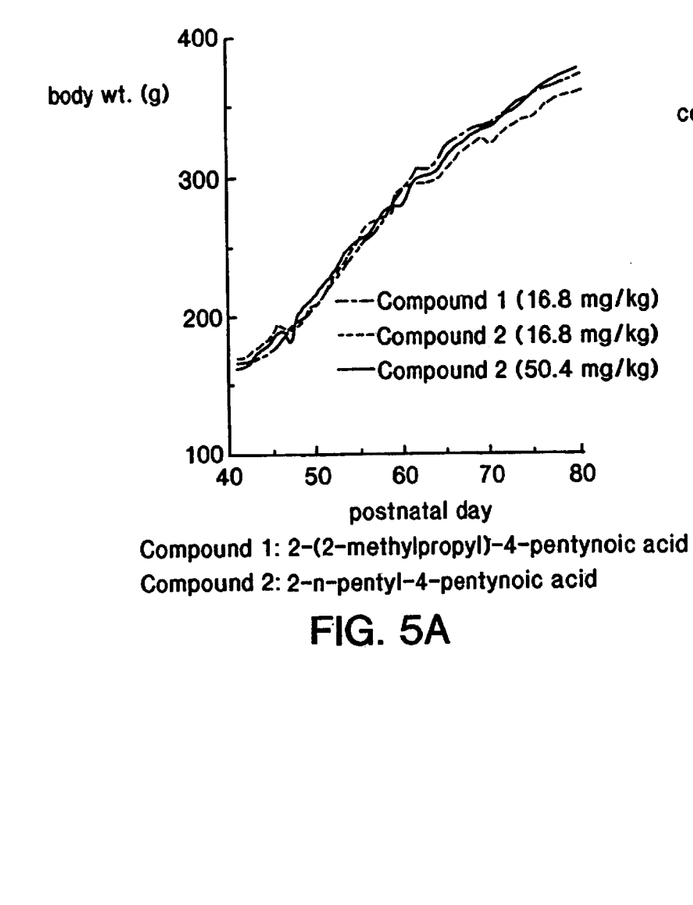
FIGS. 5A–5F: Attenuation of age-dependent decline in frequency of neural cell adhesion molecule polysialylated neurons in the hippocampal dentate gyrus and rhinal cortex by 2-n-pentyl-4-pentynoic acid. The 2-n-pentyl-4-pentynoic acid was administered chronically for 40 days at the doses indicated. The control animals received 2-(2-methylpropyl)-4-pentynoic acid. Chronic administration of these compounds had no effect on weight gain of the animals. The results are expressed as the mean ±SEM (n=6).
Figure 5B:
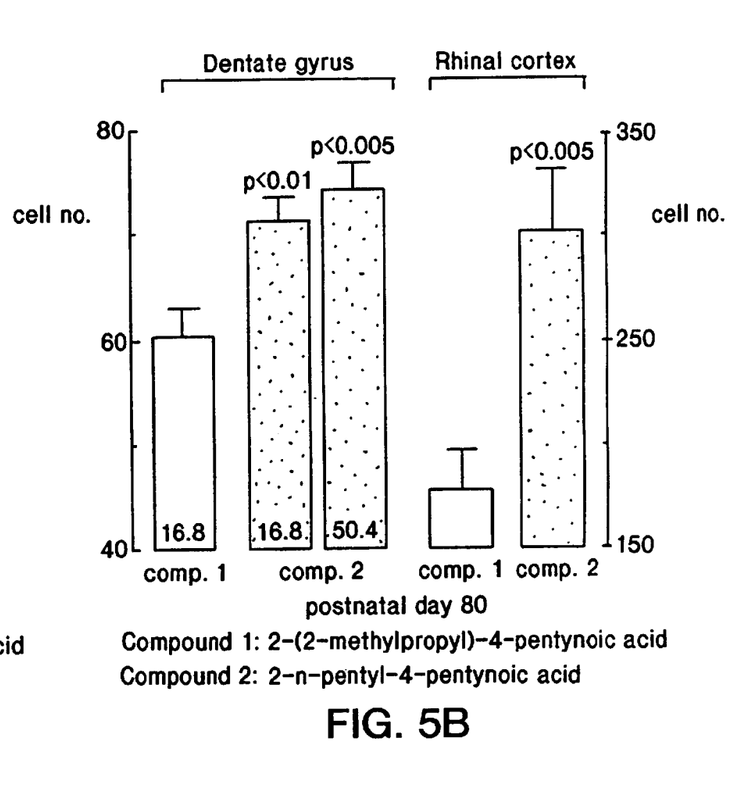
Figure 5C:
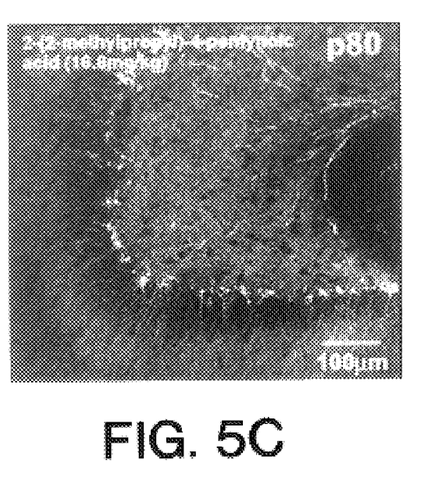
Figure 5D:
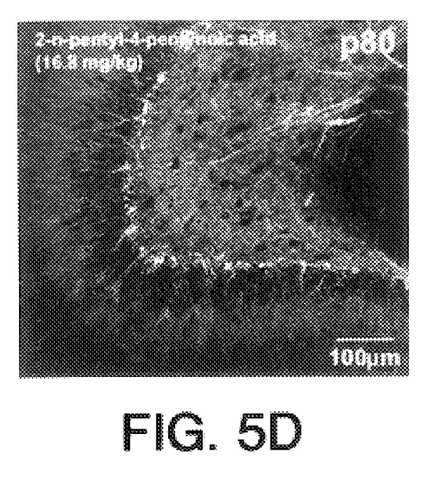
Figure 5E:
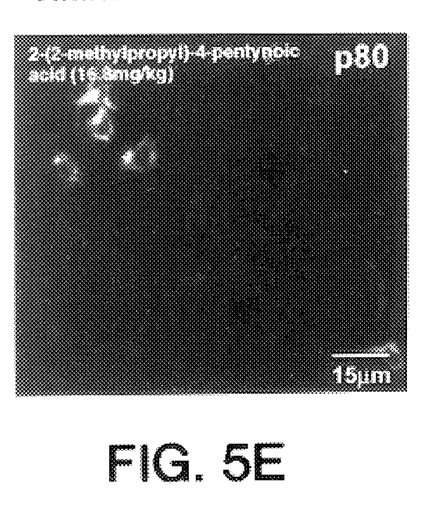
Figure 5F:
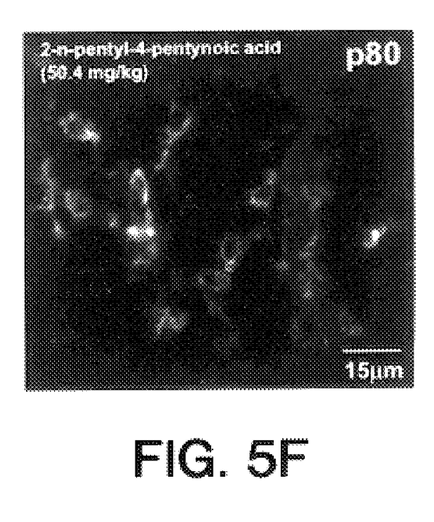

All animals, receiving vehicle only, exhibited good recall with a median latency value of 300 seconds to enter the dark, shock compartment, indicating good acquisition of the avoidance task (FIG. 4). Scopolamine administered at 6 hours post-training attenuated recall at 24 hours giving a median latency value of 65 seconds. This demonstrates the efficacy of this drug as a potent amnesic agent in this learning model. To assess the ability of these neurotrophic compounds to block or reduce these learning deficits, 2-n-pentyl-4-pentynoic acid was administered intraperitoneally 3 hours post-training and scopolamine at 6 hours post-training as before. 2-n-pentyl-4-pentynoic acid was seen to dose-dependently reduce the scopolamine-induced memory deficits observed at 24 hours post-training (FIG. 4). Reversal of scopolamine-induced amnesia was afforded by doses of 2-n-pentyl-4-pentynoic acid in the dose range of 50.4–134 mgs/kg with a highly significant reversal being observed with a dose of 84 mg/kg. No adverse effects were observed at this dose. When 134.0 mg/kg was administered, the attenuation of scopolamine-induced amnesia was greater but more variable. In the three remaining groups dosed with 2-n-pentyl-4-pentynoic acid and vehicle only, the anti-amnesic effect plateaued only at the highest concentration (134 mg/kg) tested. This was due to variation in the animals' recall ability suggesting a possible bell-shaped dose-response effect as no variation in locomotor activity was observed.

The chronic studies evaluated the ability of these compounds and compositions to spare an age-dependent decline in a population of neural cell adhesion molecule polysialylated neurons located to the granule cell layer/hilar border of the hippocampal dentate gyrus. The frequency of activated polysialylated neurons in this region increases dramatically during memory formation, and, conversely, declines with ageing when memory deficits become pronounced (Fox and Regan, Neurochem. Res. 1995 20: 521–526). As a consequence, they may be considered to be an index of memory-associated neuroplastic potential. Chronic intraperitoneal administration of 2-n-pentyl-4-pentynoic acid at 16.8 and 50.4 mgs/kg over the postnatal day 40–80 period, when an approximate 70% natural decline in the number of polysialylated neurons is observed, produced a significant sparing when compared to the control animals which received 16.8 mg/kg of 2-(2 methylpropyl)-4-pentynoic acid, which is without the antiproliferative and prodifferentiative effect seen with 2-n-pentyl-4-pentynoic acid (FIG. 5). This sparing amounted to approximately 25% at 50.4 mgs/kg, the highest dose evaluated, which represents approximately 2.5 years in human terms. In addition, polysialylated neurons were observed in the entorhinal cortex and extended, as a single band, through perirhinal cortex up to the level of the piriform cortex. This cortical cell population exhibited an approximate 2-fold sparing and/or activation following exposure to 50.4 mgs/kg of 2-n-pentyl-4-pentynoic acid over the postnatal day 40–80 period when compared to the control animals which received 16.8 mgs/kg of 2-(2-methylpropyl)-4-pentynoic acid (FIG. 5).

Figure 6:
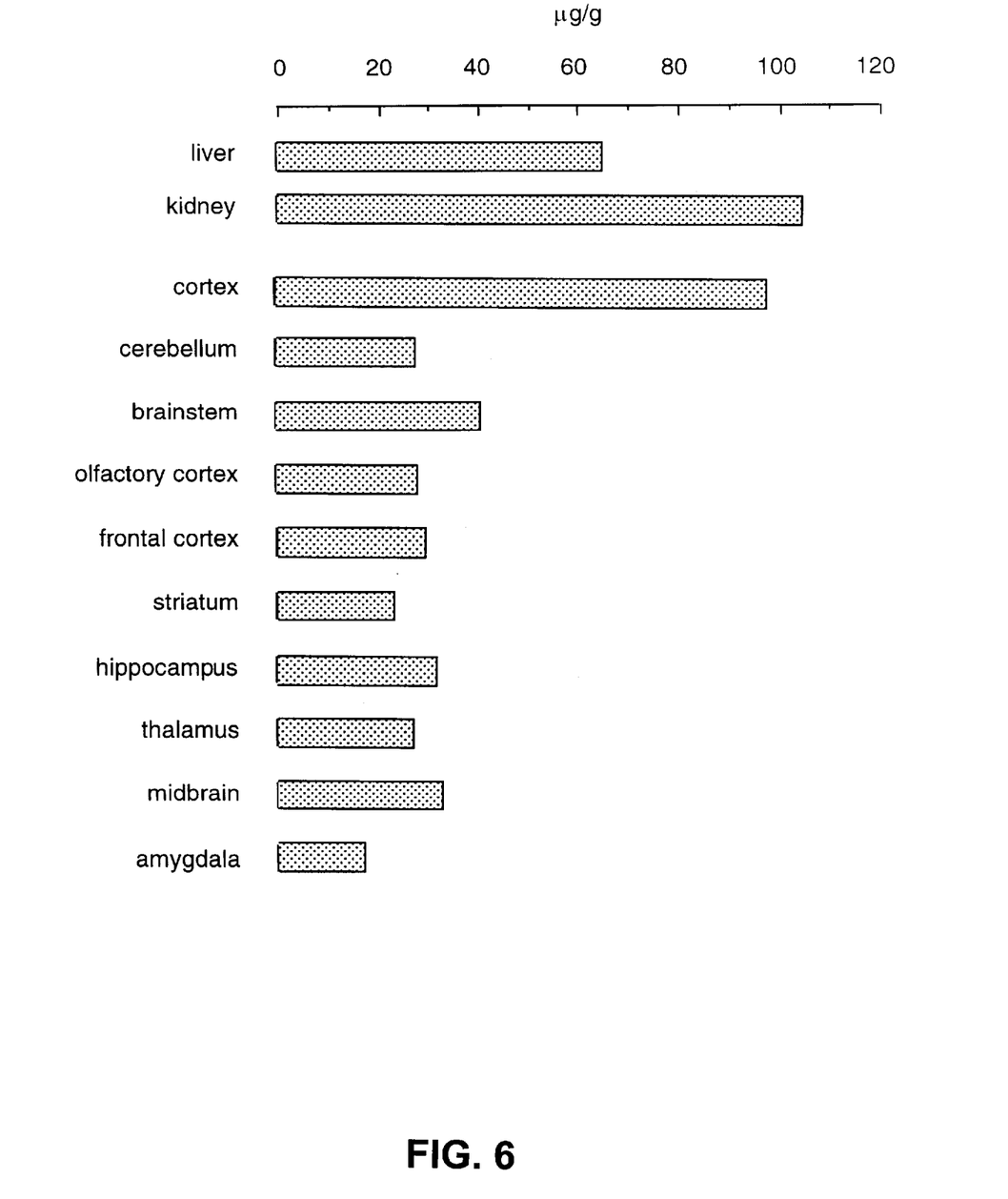
FIG. 6: Distribution of 2-n-pentyl-4-pentynoic acid in individual brain regions and in the kidney and liver. The 2-n-pentyl-4-pentynoic acid was administered by the intravenous route (84 mgs/kg) once daily for 10 days. The animals were sacrificed 30 mins following final administration of the drug. Tissue concentrations of 2-n-pentyl-4-pentynoic acid were determined by gas chromatographic selective ion monitoring mass spectrometry. The results represent a single animal experiment.

The dramatic sparing and/or activation of the polysialylated neurons in the rhinal cortex may be related to the differential distribution of 2-n-pentyl-4-pentynoic acid into the cortex as opposed to the other brain regions. In a single animal experiment, an intravenous bolus of 2-n-pentyl-4-pentynoic acid (84 mgs/kg) exhibited a 2–4 fold greater distribution to the cortex as compared to the other brain regions examined (FIG. 6). This cortical penetration was equivalent to that observed in the kidney. In addition, analysis of the plasma indicated the free concentration of 2-n-pentyl-4-pentynoic acid to be approximately 60 µg/gm corresponding to an unbound fraction of 20%.

No adverse effects were seen at either dose as indicated by an invariant weight gain between the animal groups (FIG. 5) and lack of any abnormal behaviour in open-field observations.

Passive Avoidance Training

A one-trial, step-through, light-dark model was developed and validated for learning/memory studies. The apparatus consisted of a box measuring 300 mm wide×260 mm deep×270 mm high. The front and top were transparent, allowing the experimenter to observe the behaviour of the animal inside the apparatus. The box was divided into 2 compartments, separated by a central shutter which contained a small opening 50 mm wide and 75 mm high. The smaller of the compartments measured 90 mm in width and contained a low power (6v) illumination source—the light compartment. The larger compartment measured 210 mm in width and was not illuminated.

The floor in this dark compartment consisted of a grid of 16 horizontal stainless steel bars which were 5 mm in diameter and 12.5 mm apart. A current generator was used to supply 0.75 mA to the grid floor, scrambled once every 0.5 seconds across the 16 bars. A resistance range of 40 to 60 kOhms was calculated for a group of rats (250–350g) and the apparatus calibrated accordingly. An electronic circuit detecting the resistance of the animal ensured an accurate current delivery by automatic variation of the voltage with change in resistance.

Animals were introduced to the test holding room 3 days prior to the commencement of all studies to allow time for adjustment to the new environment. After this period, animals were handled for 2 minutes for 3 days under low level red light illumination. After each handling session, the animal was weighed and placed in the open field arena where ambulation and general behaviour was assessed. On the fourth day—training day—each rat was handled, weighed and assessed in the open field arena as before. However, following behavioral assessment, the animal was placed in to the small, light compartment of the passive avoidance training apparatus so that it faced the rear wall. The door was quickly and carefully closed.

Once the rat turned around to face the front panel of the compartment (after an adaption time of usually less than 30 seconds) a timer was started and the latency to enter the larger dark compartment recorded. This time was usually less than 20 seconds. Once the animal entered the dark compartment, with all four paws on the steel grid floor, a current of 0.75 mA was delivered remotely to the floor bars. A maximum shock time of 5 seconds was set and the animal almost always returned to the safe, light compartment within this time, known as the escape latency.

The escape latency was recorded for each rat and the animal returned to its home cage immediately. A control group of animals received no footshock but were allowed to explore the apparatus for a time which was paired with one of the shocked animals. Between each training session, both compartments were wiped down thoroughly to reduce the possibility of confounding olfactory cues.

The animals were then tested for recall—or the ability to remember not to go through to the dark compartment—at 24 hours following raining. Animals were handled, weighed and assessed as before and once again placed into the safe compartment. Once the animal turned to face the front panel, the timer was started and the latency to enter the dark compartment by head only, front two paws and finally all four paws was recorded. No current was applied to the bars and a cut-of or criterion time of 5 minutes was allowed before the animal was removed and returned to its home cage. The time taken for all four of the animals' paws to enter the dark compartment was used as the basic assessment of the ability of the animal to remember and at least 6 animals per group were used to produce median and percentile ranges. A Mann-Whitney U-test for non-paramatric data estimated significance between groups.

Open Field Behaviors

Open field studies formed an essential part of the passive avoidance training. The open field apparatus was constructed out of black-painted wood 620 mm length×620 mm breadth×150 mm high. The white-painted floor of the apparatus was ruled from side to side every 77 mm dividing it into a series of boxes 77x×77 mm sq. Each animal was placed into the centre of the arena and allowed to move to a side of the apparatus at which point a timer was started. As a measure of locomotor activity, the number of lines crossed over the next 5 minutes was counted .

Other behaviour assessed included rearing, grooming, piloerection, defecation and posture—all being a good indication of the state of health of the animal. body weight was noted as a matter of course. All observations were carried out in the quiet room under low-level illumination between 08.00 and 14.00 to minimise circadian influence. This behavioral assessment was invaluable for detecting animals not responding to the training schedule or unwanted interventive effects which may confound test results.

Immunohistochemistry.

The frequency of neural cell adhesion molecule polysialylated neurons at the granule cell layer/hilar region of the hippocampal dentate gyrus was established by immunohistochemical techniques. Freshly dissected brains were coated immediately in an optimal cutting temperature compound (Gurr, U.K.), snap-frozen in liquid nitrogen-cooled n-hexane and stored at −80° C. until required for further processing. Horizontal cryostat sections of 12 $\mu$m were cut from frozen tissue using a MICROM (Series 500) cryostat. Serial sections were obtained for analysis from the same point which was mid-way down the septo-temporal axis (equivalent to −5.6mm from Bregma for analysis of dentate cells and −8.10 mm from Bregma for analysis of cortical cells (Paxinos and Watson, *The Rat Brain in Stereotaxic Coordinates*, Academic Press, 1986)) and thaw-mounted onto 0.1% (w/v) poly-1-lysine coated glass slides. The sections were fixed in 70% (v/v) ethanol for 30 min, washed twice for 10 min in a washing buffer of 0.1M phosphate buffered 0.9% saline, pH7.4, (PBS) and incubated overnight (20 hours) in a humidified chamber at room temperature with anti-NCAM-PSA (Rougon et al., J. Cell Biol. 1986 103:2429–2437) diluted 1:500 in an incubation buffer composed of PBS containing 1% (w/v) bovine serum albumen (Sigma Chemical Co., U.K.) and 1% (v/v/) normal goat serum (DAKO, Denmark) in order to eliminate non-specific staining. The sections were washed again and exposed for 3 hours to fluorescein-conjugated goat anti-mouse IgM (Calbiochem. U.K.) diluted 1:100 with incubation buffer. The sections received a final wash before being mounted in Citifluor$^R$ (Agar, UK), a fluorescence-enhancing medium. The staining pattern was observed with a Letiz DM RB fluorescence microscope using an exciting wavelength of 495 nm and an emitting wavelength of 525 nm. Immunofluorescence staining was specific as it was eliminated completely by omission of either the primary of secondary antibody and by preabsorbing anti-NCAM-PSA with colominic acid (1 mg/ml; Sigma Chemical Co., U.K.). which contains α2,8 homopolymers of sialic acid. Where relevant, sections were counter-stained by a brief exposure (60 seconds) to propidium iodide (40 ng/ml PBS) which was detected using an excitation wavelength of 552 nm and an emission wavelength of 570 nm.

The total number of NCAM-PSA-immunoreactive neurons in the dentate granule cell layer and at the hilar border were counted in ten alternate 12 μm sections, to preclude double counting of the 5–10 μm perikarya, divided by the total area of the granule cell layer, which included all propidium iodide labelled cells, and multiplied by the average granule cell area which was 0.15±0.01 $mm_2$ at this level, and the mean±sem for each animal group calculated. These means were used to establish the mean±sem for each animal group. Area measurements were performed using a Quantimet 500 Image Analysis System. Statistical analysis employed the Students' t-test.

GC-MS Analysis of 2-n-pentyl-4-pentynoic Acid

An indwelling cannula (0.5 mm internal diameter) was placed into the left jugular vein under sodium pentobarbitone (60 mgs/kg) anaesthesia, 4 days prior to drug administration. The cannula was maintained patent with 20% polyvinylpyrrolidone containing 50 units/ml heparin and flushed twice daily. A bolus of 2-n-pentyl-4-pentynoic acid 84 (mg/kg) was administered once daily for 10 days. The animal was sacrificed 30 mins following final administration of the drug, the brain was removed, dissected into individual regions, placed in pre-weighed vials and stored frozen at −80° C. until required. The liver and kidney were treated in a similar manner. The blood was obtained by cardiac puncture, collected into heparinised tubes and the plasma prepared by centrifugation at 1500 rpm for 10 min. The supernatant was aliquoted and stored frozen in pre-weighed vials.

To extract the 2-n-pentyl-4-pentynoic acid, the tissue was homogenised by ultrasonication into 2–10 vols $H_2O$. Aliquots of 100–200 μl were extracted by the addition of 50 μl of 1N $NaH_2PO_4$ buffer (pH 5.0) and 1 ml of ethylacetate containing 1 μg/ml 2-methyl-2-ethylhexanoic acid as an internal standard. The mixture was shaken for 15 min, centrifuged for 1 min and the supernatant concentrated to approximately 200 μl by a stream of nitrogen at 20° C. and a 100 μl aliquot of acetonitrile added. The extraction was repeated with ethylacetate alone and the combined extracts evaporated to a final volume of 10–20 μl. Trimethylsilylation was accomplished by addition of 30 μl of pyridine and 30 μl of N-methyl-N-trimethylsilyl-trifluoroacetamide at room temperature for at least 30 min and 1 μl aliquots were injected into the gas chromatographic-mass spectrometer (GC-MS). Unbound 2-n-pentyl-4-pentynoic acid was measured after ultrafiltration of serum aliquots with the Amicon MPS-1 Ultrafiltration advice (YMT-membrane, cut-off 30 kDa). GC-MS analysis was carried out using a Perkin-Elmer F22-9-C, coupled via a Jet separator to a Finnigan MAT CH-7-A mass spectrometer operated by a 2100D Superincos. A fused silica Megabore column was used (30 m×0.53 mm internal diameter, 1 μm film thickness), coated with DB1701. The temperature of the injector was held at 220° C. The initial over temperature was 80° C. After injection, the temperature was held at 80° C. for 1 min, rapidly raised to 120° C., and then at a rate of 4° C./min to 190° C. Detection took place in the selective ion monitoring mode with the following ions: m/z 225 for 2-n-pentyl-4-pentynoic acid and ion m/z 215 for the 2-methyl-2-ethylhexanoic acid internal standard. Linear calibration graphs were used to determine the individual tissue concentrations.

EXAMPLE 7

Teratogenicity of Valproic Acid and Valproic Acid-Related Carboxylic Acids

The teratogenicity of valproic acid and valproic acid-related carboxylic acids with variations in the length of one side chain in NMRI mice was determined. Tables 1 and 2 set forth the results for the following compounds: VPA (valproic acid), ethyl-4-yn-VPA (2-n-ethyl-4-pentynoic acid), 4-yn-VPA (2-n-propyl-4-pentynoic acid), butyl-4-yn-VPA (2-n-butyl-4-pentynoic acid), pentyl-4-yn-VPA (2-n-pentyl-4-pentynoic acid) and hexyl-4-yn-VPA (2-n-hexyl-4-pentynoic acid). Each carboxylic acid compound was administered in doses of mmol sodium salt/kg. The embryolethality values reflect a percentage of total implants, and the exencephaly values reflect a percentage of live fetuses. The number of affected fetuses are shown in parentheses. The teratogenic effect of the carboxylic acids according to the present invention was determined by the mouse exencephaly model described by Nau in *Toxicol. Appl. Pharmacol.* 80, 243–250 (1985) and U.S. Ser. No. 08/344,810, filed Nov. 23, 1994 which is herein incorporated by reference. Female NMRI mice are mated with male NMRI mice between 6.00 and 9.00 hours. The first 24 hours after conception are regarded as day zero of gestation. The solution of the sodium salts of the carboxylic acids were injected intraperitoneally into the mice on the morning of day eight of gestation. On day 18 of gestation, between 9.00 and 12.00 hours, the animals were anesthetized with diethyl ether and subsequently the uterus was removed. The number of implantation sites and the resorptions and dead fetuses (embryolethality) was determined. Each live fetus was weighed and examined for exencephaly.

TABLE 1

| Carboxylic acid | Dose[1] (mmol/kg) | No. of litters | No. of live fetuses | Fetal weight (mean ± SD) (g) | Embryolethality[2] (%) | Exencephaly[3] (%) |
| --- | --- | --- | --- | --- | --- | --- |
| VPA | 3.0 | 8 | 60 | 1.07 ± 0.10 | 49 | 42 |
| Ethyl-4-yn-VPA | 1.85 | 6 | 73 | 1.12 ± 0.09 | 5 | 0 |
| 4-yn-VPA | 1.85 | 7 | 21 | 0.92 ± 0.12 | 76 | 81 (17) |
|  | 1.23 | 13 | 89 | 1.03 ± 0.13 | 16 | 12 |
| Butyl-4-yn-VPA | 1.85 | 8 | 27 | 0.88 ± 0.06 | 69 | 96 (26) |
|  | 1.25 | 9 | 63 | 0.99 ± 0.09 | 45 | 71 (45) |
| Pentyl-4-yn-VPA | 1.85 | 9 | 26 | 0.84 ± 0.11 | 78 | 81 (21) |
|  | 1.25 | 6 | 44 | 1.02 ± 0.09 | 40 | 60 (26) |

TABLE 1-continued

| Carboxylic acid | Dose[1] (mmol/kg) | No. of litters | No. of live fetuses | Fetal weight (mean ± SD) (g) | Embryolethality[2] (%) | Exencephaly[3] (%) |
|---|---|---|---|---|---|---|
| Hexyl-4-yn-VPA | 1.85 | 3 | 0 | — | 100 | — |
|  | 1.5 | 6 | 12 | 0.86 ± 0.07 | 84 | 100 (12) |
|  | 1.25 | 7 | 29 | 0.96 ± 0.06 | 67 | 79 (23) |
|  | 1.0 | 7 | 37 | 1.03 ± 0.05 | 54 | 70 (26) |
|  | 0.5 | 13 | 165 | 1.25 ± 0.10 | 18 | 7 (9) |
| Controls |  | 14 | 152 | 1.19 ± 0.12 | 11 | 0 |

[1]The doses are in mmol sodium salt of each carboxylic acid/kg. All substances were injected intraperitoneally on the morning of day 8 of gestation.
[2]% of total implants.
[3]% of live fetuses. Number of affected fetuses are shown in parentheses.

TABLE 2

| Substance[1] | No. of litters | Embryo-lethality | No. of live fetuses | Fetal weight (mean ± SD) (g) | Exencephaly (%) |
|---|---|---|---|---|---|
| 4-yn-VPA | 13 | 16 | 89 | 1.03 ± 0.13 | 12 |
| Butyl-4-yn-VPA | 9 | 45 | 63 | 0.99 ± 0.09 | 71 (45) |
| Pentyl-4-yn-VPA | 6 | 40 | 44 | 1.02 ± 0.09 | 60 (26) |
| Hexyl-4-yn-VPA | 7 | 67 | 29 | 0.96 ± 0.06 | 79 (23) |

[1]1.25 nmol sodium salt of each carboxylic acid per kg body weight was administered on the morning of day 8 of gestation.

While we have hereinbefore described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

We claim:

1. A pharmaceutical composition for inhibiting cell mitosis comprising an effective amount of at least one compound selected from the group consisting of 2-n-pentyl-4-pentynoic acid, enantiomers thereof and pharmaceutically acceptable salts thereof, and a pharmaceutically acceptable carrier.

2. A pharmaceutical composition for inhibiting cell mitosis comprising an effective amount of 2-(S)-2-n-pentyl-4-pentynoic acid, or a pharmaceutically acceptable salt thereof, and a pharmaceutically acceptable carrier.

3. A pharmaceutical composition for inhibiting cell mitosis comprising an effective amount of 2-(S)-2-n-hexyl-4-pentynoic acid, or a pharmaceutically acceptable salt thereof, and a pharmaceutically acceptable carrier.

* * * * *